: US006781389B1

United States Patent
Colvin et al.

(10) Patent No.: US 6,781,389 B1
(45) Date of Patent: Aug. 24, 2004

(54) CONDUCTIVITY SENSOR FOR DETECTING CONDUCTIVITY OF A FLUID

(75) Inventors: Alex David Colvin, Oak Park, MI (US); Joseph C Cassatta, Taylor, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 09/682,742

(22) Filed: Oct. 12, 2001

(51) Int. Cl.[7] .................... G01R 27/08; G01N 27/02
(52) U.S. Cl. ........................ 324/724; 324/449
(58) Field of Search ................ 324/691–727, 324/71.1

(56) References Cited

U.S. PATENT DOCUMENTS

| | | | | |
|---|---|---|---|---|
| 3,549,989 A | | 12/1970 | Brown .................. 324/443 |
| 3,866,678 A | * | 2/1975 | Jeter ................... 324/449 |
| 3,906,354 A | * | 9/1975 | Murdock ............... 324/448 |
| 3,989,009 A | | 11/1976 | Robar et al. .......... 119/14.08 |
| 3,991,623 A | * | 11/1976 | Murdock ............... 324/449 |
| 4,010,715 A | | 3/1977 | Robar et al. .......... 119/14.14 |
| 4,035,719 A | * | 7/1977 | Anderson .............. 324/444 |
| 4,255,968 A | | 3/1981 | Harpster ............... 73/204 |
| 4,365,200 A | * | 12/1982 | Goldsmith ............. 324/449 |
| 4,384,578 A | | 5/1983 | Winkler ................ 604/114 |
| 4,751,466 A | | 6/1988 | Colvin et al. .......... 324/449 |
| 4,786,875 A | * | 11/1988 | Carll ................... 73/861.15 |
| 5,025,220 A | | 6/1991 | Colvin et al. .......... 324/449 |
| 5,060,860 A | | 10/1991 | Megerle ................ 239/67 |
| 5,792,964 A | | 8/1998 | van den Berg ......... 73/861.15 |
| 5,931,802 A | * | 8/1999 | Yoshida et al. ........ 604/6.11 |
| 5,973,503 A | | 10/1999 | Kuipers et al. ......... 324/698 |
| 6,038,921 A | | 3/2000 | McMillan et al. ...... 73/204.23 |

* cited by examiner

*Primary Examiner*—N. Le
*Assistant Examiner*—Timothy J. Dole
(74) *Attorney, Agent, or Firm*—Artz & Artz, P.C.; Carlos L. Hanze

(57) ABSTRACT

A conductivity sensor (16) and control circuit (18) for determining the conductivity of a fluid is provided. Conductivity sensor (16) is formed of a first annular electrode (24) spaced apart from a second annular electrode (26) having a tubular portion (28) therebetween. The first annular electrode (24) and the second annular electrode (26) are coupled to a control circuit (18). The control circuit (18) preferably includes a square wave generating circuit (40), a current-to-voltage converter circuit (42) coupled to one of the electrodes, a buffer circuit (44) coupled to the other one of the electrodes, a synchronous detector circuit (46). The synchronous detector circuit (46) is operated using the square wave from square wave generator circuit (40). By oscillating between a negative and positive gain, a constant direct current output corresponding to the conductivity of the fluid between the first annular electrode and second annular electrode is provided.

20 Claims, 3 Drawing Sheets

CONDUCTIVITY SENSOR FOR DETECTING CONDUCTIVITY OF A FLUID

CROSS REFERENCE TO RELATED APPLICATIONS

The present invention is related to application entitled "Control Circuit for Operating a Conductivity Sensor and Method Therefor", having U.S. Ser. application No. 09/682,740, filed simultaneously herewith on Oct. 12, 2001, and incorporated by reference herein.

BACKGROUND OF INVENTION

The present invention relates generally to conductivity sensors, and more specifically to conductivity sensors suitable for detecting relatively low conductivity.

Fuel cells are increasingly being investigated as an alternative power source for automotive vehicles. Fuel cells generate electricity using a membrane. The process also generates heat. Fuel cells therefore must be cooled by circulating coolant therethrough. In automotive applications, the coolant may be a mixture of ethylene glycol and water. Fuel cells, however, are sensitive to the conductivity of the coolant. If the conductivity is too high, the coolant should be changed to allow the fuel cell to operate efficiently. Therefore, a means for sensing the conductivity to allow a warning to the vehicle operator so that the fluid may be changed is necessary.

Known configurations for conductivity sensors include multiple electrodes that are used to sense the conductivity therebetween. Known sensors are unable to adequately detect low conductivities. Another drawback to providing a conductivity sensor is the space within a fuel cell vehicle is scarce. Therefore, a small conductivity sensor should be provided so that the package size of the vehicle does not need to be increased. Another problem with fuel cell vehicles is that the fuel cell compartment is an electrically noisy environment. This can cause erroneous readings using known electrical conductivity sensors.

It would therefore be desirable to provide a conductivity sensor that has a small package size, allows detection of low conductivity fluids and is capable of performing in an electronically noisy environment.

SUMMARY OF INVENTION

The present invention provides an improved conductivity sensor particularly suited for low conductivity detection. The present invention includes a conductivity sensor having a first annular electrode having a first inner diameter and a second annular electrode having the first inner diameter. A tubular portion is positioned axially between the first electrode and the second electrode. The tubular portion has a second inner diameter greater than the first inner diameter between the first electrode and the second electrode.

In a further aspect of the invention, a method of assembling a conductivity sensor comprises:

coupling a first annular electrode having a first inner diameter to a tubular portion;

coupling a second annular electrode having the first inner diameter to the tubular portion so that the tubular portion positioned axially between said first electrode and said second electrode.

One advantage of the invention is that the sensor and control circuit according to the present invention is capable of measuring extremely low conductivity in fluids. Another advantage of the invention is that the sensor may be coupled within a fluid path and therefore take very little space. Yet another advantage of the invention is that because a synchronous detector is used in the control circuit, the circuit is not prone to errors due to electrical noise.

Other advantages and features of the present invention will become apparent when viewed in light of the detailed description of the preferred embodiment when taken in conjunction with the attached drawings and appended claims.

DETAILED DESCRIPTION

Figure 1:
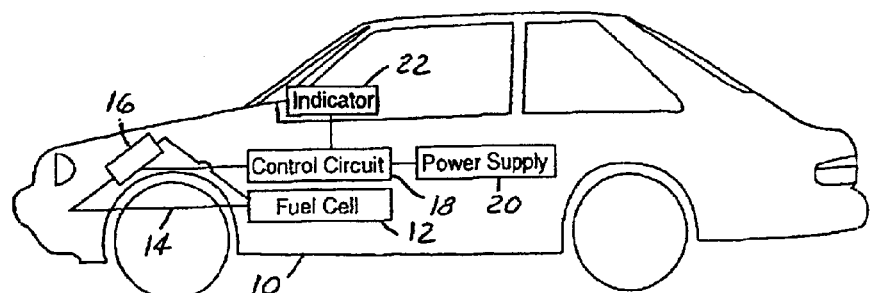
FIG. 1 is a block diagrammatic view of an automotive vehicle having a sensor and control circuit according to the present invention.

In the following figures the same reference numerals are used to identify the same components. The present invention is described with respect to a coolant path for a fuel cell powered vehicle. However, those skilled in the art will recognize various other applications for the sensor according to the present invention.

In the following description several specific values have been specified. These values are meant as examples only and are not meant to be limiting.

Referring now to FIG. 1, an automotive vehicle 10 has a fuel cell 12 therein. Fuel cell 12 has a coolant path 14 formed of tubular material. Coolant path 14 has a conductivity sensor 16 coupled in series therewith. A control circuit 18 is coupled to conductivity sensor 16. Control circuit 18 controls the operation of sensor 16 in that control circuit 18 can determine the conductivity of the fluid passing through coolant path 14 in response to the output of conductivity sensor 16.

Control circuit 18 is coupled to power supply 20 and to an indicator 22. Indicator 22 may comprise various types of indicators including vehicle warning lights, an audible indicator such as a bell or chime or other types of indicators such as a meter. Indicator 22 is used to communicate the conductivity sensed by sensor 16 and control circuit 18 to the vehicle operator. In a fuel cell application as shown, the driver may be signaled as part of a driver warning system to the composition of the coolant fluid. That is, if the conductivity rises above a certain point, the driver may be signaled to replace the coolant.

Figure 2:
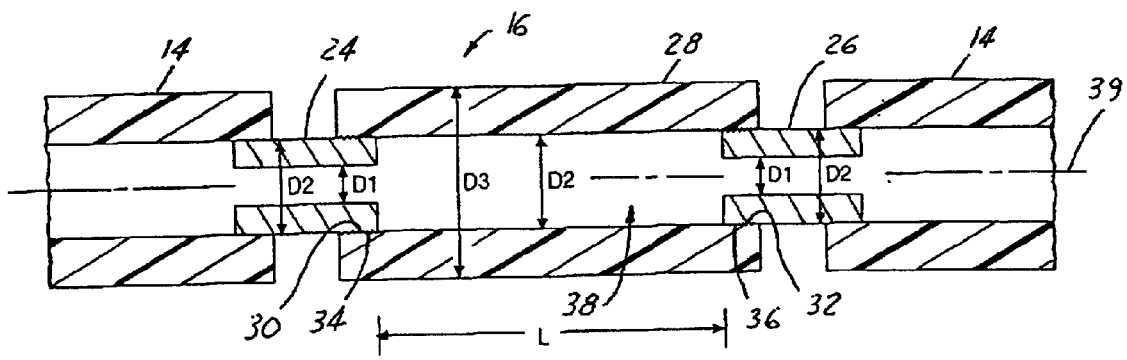
FIG. 2 is a cross-sectional view of a sensor according to the present invention.

Referring now to FIG. 2, sensor 16 is illustrated in further detail coupled within coolant path 14. Although a simple interference connection is illustrated between coolant path 14 and sensor 16, other types of connects and quick disconnects may be provided. Sensor 16 is formed of a first annular electrode 24 and a second annular electrode 26. First annular electrode 24 and second annular electrode 26 are preferably configured in a similar manner. First annular electrode 24 and second annular electrode 26 are spaced apart from each other and have a tubular portion 28 therebetween.

First annular electrode 24 and second annular electrode 26 are coupled to coolant path 14. Coolant path 14 is preferably formed of a non-electrically conductive material. Preferably, first annular electrode 24 and second annular electrode 26 are formed of a highly electrically conductive material such as stainless steel. First annular electrode 24 and second annular electrode 26 have an inner diameter $D_1$ and an outer diameter $D_2$. Both the first annular electrode 24 and second annular electrode 26 are configured similarly and preferably have the same diameters.

Tubular portion 28 is preferably formed of a non-conductive material. Tubular portion 28 has an inner diameter $D_2$ the same as the outer diameter of first annular electrode 24 and second annular electrode 26. Tubular portion 28 also has an outer diameter $D_3$.

First annular electrode 24 and second annular electrode 26 may be coupled to tubular portion 28 in an interference fit. However, a threaded portion 30, 32 on respective first annular electrode 24 and second annular electrode 26 may be included. Threaded portions 30, 32 correspond with threaded portions 34, 36 on the inside diameter of tubular portion 28. To ease assembly, the first annular electrode 24 and second annular electrode 26 may be screwed into tubular portion 28.

Once assembled, a cell 38 is defined between first annular electrode 24, second annular electrode 26 and the inner diameter of $D_2$ of tubular portion 28. Once the electrodes 24, 26 are coupled to tubular portion 28, the electrodes 24, 26 are spaced by a distance L which corresponds to the length of cell 38. The cell constant is thus defined by the formula.

$$\pi D_2^2/4L$$

where $D_2$ is the inner diameter of tubular portion 28 and L is length of the cell 38.

Preferably, each of the electrodes 24, 26 and tubular portion 28 is aligned along the same longitudinal axis 39. That is, electrodes 24, 26 and tube portion 28 are coaxial.

To further increase the reliability of the system a seal material may be positioned between first annular electrode 24 and tubular portion 28 and between second annular electrode 26 and tubular portion 28. One type of suitable material is a thread-seal tape, such as Teflon tape, which may be positioned on threaded portions 30, 32, 34, and 36. Because the cell constant is well defined, a known resistor used within he calibration circuit as will be further described below, may be used to calibrate the system.

Figure 3:
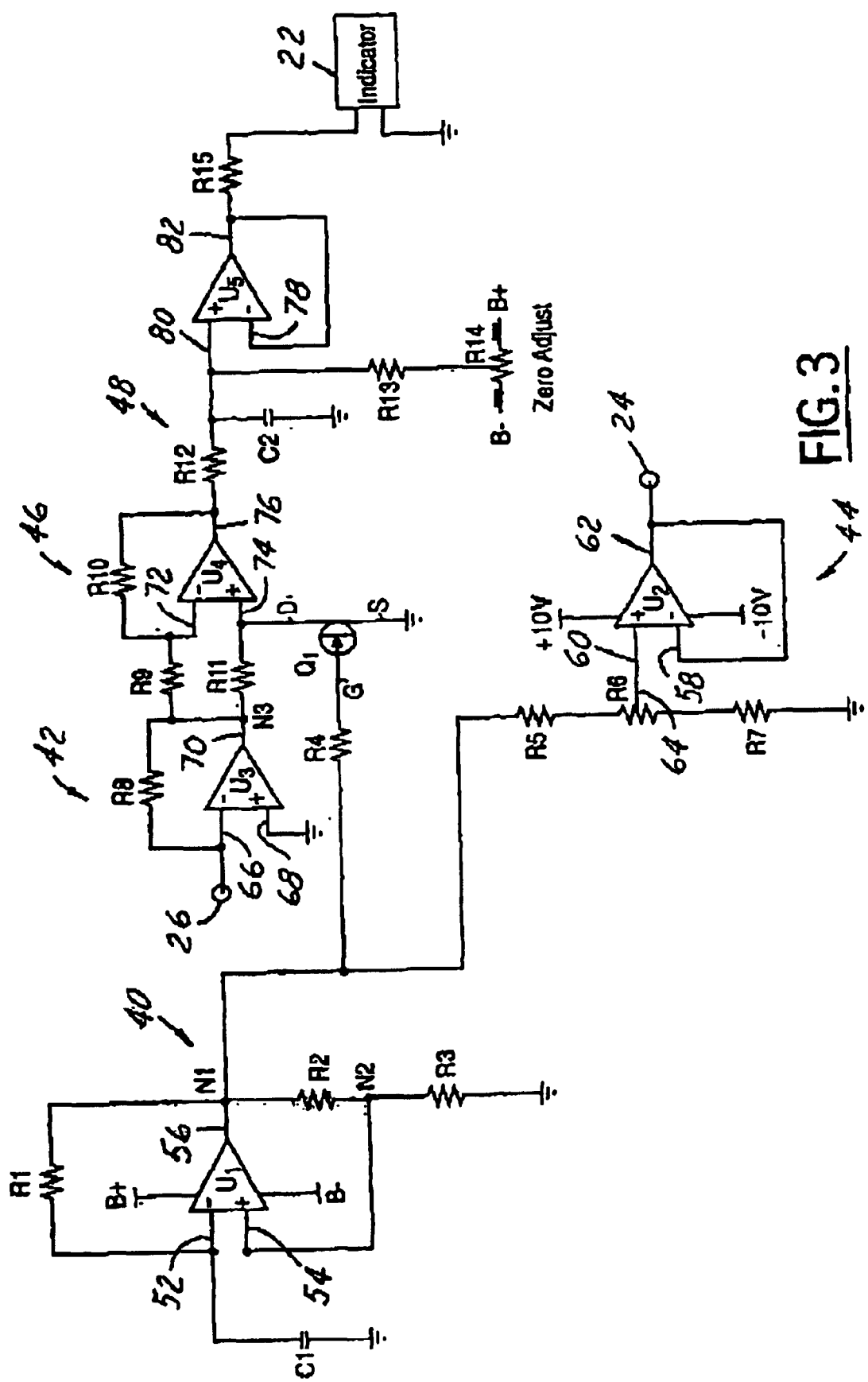
FIG. 3 is a schematic view of the control circuit of the present invention.

Referring now to FIG. 3, control circuit 18 is illustrated in further detail. First annular electrode 24, second annular electrode 26 and indicator 22 are diagrammatically illustrated. Control circuit 18 generally has a square wave generator circuit 40, a current-to-voltage converter 42, a buffer circuit 44, and a synchronous detector circuit 46. The output of the device may also be filtered in a filter circuit 48. The conductivity may also be adjusted in zero adjustment circuit 50. The output of the control circuit 18 is a voltage corresponding to the conductivity of the liquid between first annular electrode 24 and second annular electrode 26.

Square wave generator circuit 40 may, for example, produce a square wave of about 300 Hz. Although various types of square wave generating cots may be used, an operational amplifier-based circuit is illustrated. Square wave generator circuit 40 has an operational amplifier $U_1$ having an inverting input 52, a non-inverting input 54, and an output 56. A capacitor $C_1$, which in this case is 0.015 $\mu$F is coupled to inverting input 52. A resistor $R_1$ is coupled between inverting input 52 and output 56. Output 56 is coupled to ground through a first resistor $R_2$ and $R_3$. The node between $R_2$ and $R_3$ is common node $N_2$. Common node $N_2$ is coupled to non-inverting input 54. The common node at output 56 is coupled to synchronous detection circuit through resistor $R_4$. Each of the resistors $R_1$, $R_2$, $R_3$ and $R_4$ in this example is 100 k$\Omega$. Buffer circuit is also formed of an operational amplifier $U_2$. Operational amplifier $U_2$ has an inverting input 58, a non-inverting input 60, and an output 62. Output 62 is coupled to fist annular electrode 24, which in turn is coupled to inverting input 58. Node $N_1$ is coupled to ground through three resistors $R_5$, $R_6$ and $R_7$. In the present example, $R_5$ is 68 k$\Omega$ and $R_7$ is 2.2 k$\Omega$ $R_6$ is a 5 k$\Omega$ potentiometer having an adjustable terminal 64 coupled to non-inverting input 60. As will be further described below, the conductivity gain adjustment may be provided through adjustment of the adjusting terminal 64 of resistor $R_6$.

Current-to-voltage converter 42 is also formed of an operational amplifier $U_3$. Operational amplifier $U_3$ has an inverting terminal input 66, a non-inverting input 68, and an output 70. Inverting terminal 66 is coupled to second annular electrode 26. Non-inverting input 68 is coupled to ground. Output terminal 70 is coupled to inverting input 66 through a resistor $R_8$. A common node $N_3$ is coupled to output terminal 70.

Synchronous detector circuit 46 is also preferably formed of an operational amplifier $U_4$. Operational $U_4$ has an inverting input terminal 72, a non-inverting input terminal 74, and an output terminal 76. Inverting input terminal 72 is coupled to a resistor $R_9$ which in turn is coupled to common node $N_3$. Inverting input 72 is also coupled to output terminal 76 through a feedback resistor $R_{10}$. Non-inverting input 74 is coupled to common node $N_3$ through resistor $R_{11}$. In this circuit, each of the resistors $R_9$, $R_{10}$, and $R_{11}$ are 20 k$\Omega$. Non-inverting input 74 is also coupled to a switch $Q_1$. Gate $Q_1$ has a gate G terminal, a source S terminal, and a drain D terminal. Drain terminal D is preferably coupled to non-inverting input, gate is coupled to resistor $R_4$, and source is coupled to ground. Switch $Q_1$ is illustrated as a field effect transistor. However, those skilled in the art will recognize that other types of switches may be used. Output 76 of synchronous detection circuit 46 is coupled to filter circuit 48. Filter circuit 48 comprises a first resistor $R_{12}$ and a capacitor $C_2$. Resistor $R_{12}$ is preferably 100 k$\Omega$ and capacitor $C_2$ is preferably one $\mu$F. In many applications, a filter circuit may not be required. However, the addition of a filter circuit may improve the conductivity detection. The output of filter circuit 48 is coupled to a zero adjustment circuit 50. Zero adjustment circuit 50 also preferably has an operational amplifier $U_5$. Operational amplifier $U_5$ has an inverting input 78, a non-inverting input 80, and an output terminal 82. Inverting input 78 is preferably coupled to output 82. Non-inverting input 80 is preferably coupled to a resistor $R_{13}$ which in turn is coupled to an adjustable resistor $R_{14}$. $R_{13}$ may be 2.2M$\Omega$ and potentiometer $R_{14}$ may, for example, be 100 k$\Omega$ max. As will be further described below, zero adjustment circuit 50 may be used when no fluid is present in the cell 38. When the terminals 24 and 26 thus are not electrically connected through any fluid, a zero adjustment may be made by adjusting the potentiometer $R_{14}$ which is in turn connected to positive battery voltage plus 15 volts and negative battery voltage minus 15 volts. The output of zero adjustment circuit 82 is coupled to a resistor $R_{15}$ which in turn is coupled to indicator 22.

Figure 4:
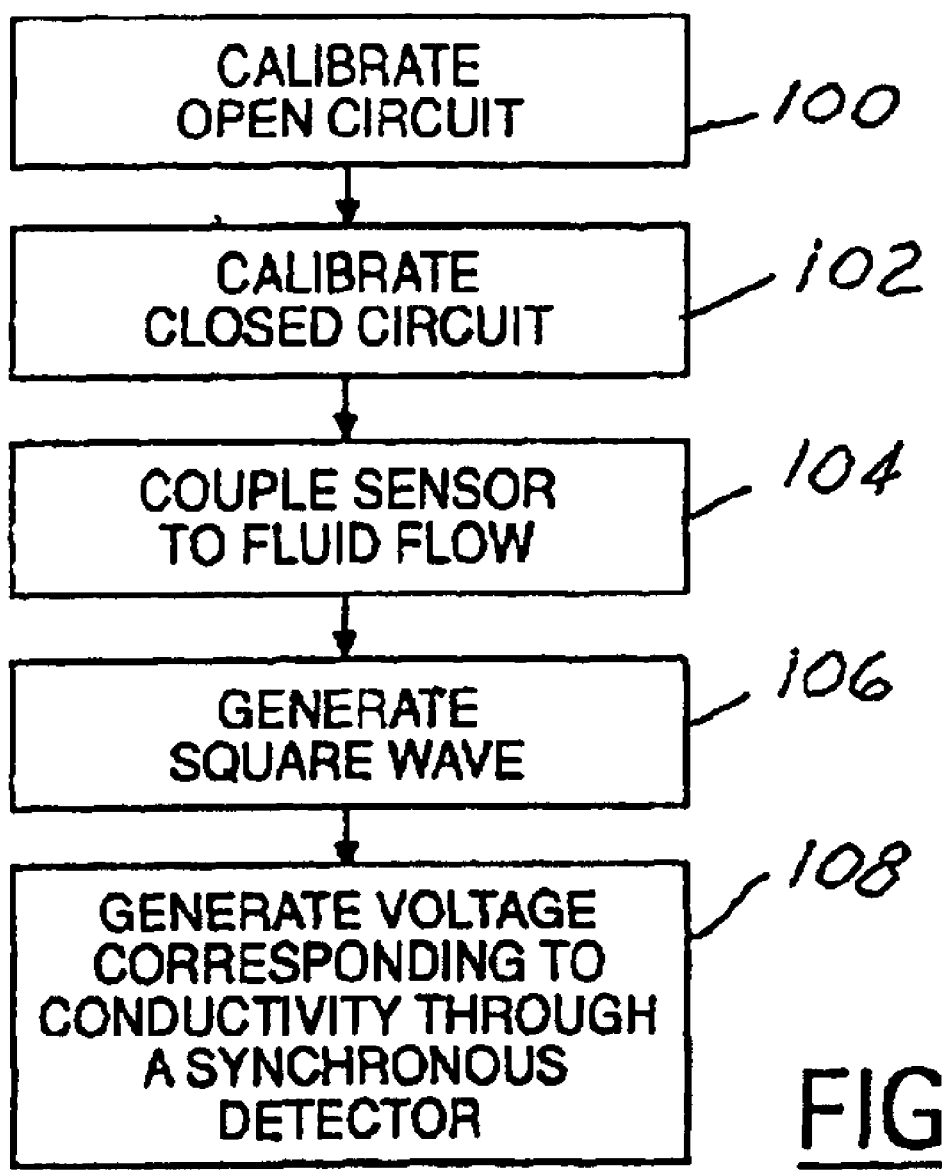
FIG. 4 is a flow chart of the operation of the present invention.

Referring now to FIGS. 3 and 4, the circuit may be operated by forming an open circuit between first annular electrode 24 and second annular electrode 26 by providing no fluid therebetween. The open circuit is calibrated in step 100 by adjusting the potentiometer $R_{14}$ so that the indicator 22 indicates no conductivity. This step is advantageous from the previously known sensors. In step 102, the closed circuit is calibrated. That is, a resistor may be coupled between first annular electrode 24 and second annular electrode 26 that corresponds to the cell constant described above. By knowing the cell constant a suitable resistor may be chosen so that the conductivity gain adjustment may be performed by adjusting potentiometer $R_6$. After calibration, the circuit may then be operated. That is, in step 104 fluid may be passed through the sensor and the sensor is coupled to the fluid flow. In step 106, square wave generator 40 generates a square wave which in turn operates switch $Q_1$. The current-to-voltage converter 42 and synchronous detector circuit 46 use the square wave generated at the square wave generator circuit 40 as a reference signal. That is, the synchronous detector oscillates between an amplifier gain of −1 and +1. Correspondingly, switch $Q_1$ acts as a short half the time. That is, when switch $Q_1$ is open, non-inverting input 74 is at the same voltage as output terminal 70 of operational amplifier $U_3$. This forces inverting input 72 to be the same voltage. That is, at this time there is no current through resistors $R_8$ and $R_{11}$ while operational amplifier $U_4$ is at a gain of +1.

When switch $Q_1$ is closed, the non-inverting input 74 to operational amplifier $U_4$ is essentially shorted to ground and thus the output of the amplifier $U_4$ is −1. Thus, by providing the alternating input a direct current output corresponding to the conductivity is provided through synchronous detector circuit 46 in step 108. Advantageously, once the circuit has been adjusted for a particular circuit, it is believed that little or not adjustment may be required during the operation. Also, because of the way the synchronous detector circuit 46 operates, the circuit essentially averages out any electrical noise in the system. Another advantage of the invention is that because of the small size and serial aspect of the sensor, little space is taken by this device.

While particular embodiments of the invention have been shown and described, numerous variations and alternate embodiments will occur to those skilled in the art. Accordingly, it is intended that the invention be limited only in terms of the appended claims.

What is claimed is:

1. A conductivity sensor comprising:

a first annular electrode having a first inner diameter and a first outer diameter;

a second annular electrode having the first inner diameter and the first outer diameter; and a tubular portion disposed axially between said first electrode and said second electrode, said tubular portion defining a sensor cell with said first annular electrode and said second annular electrode;

said cell having a second inner diameter substantially equal to the first outer diameter that is greater than said first inner diameter and a cell length between said first electrode and said second electrode;

said first electrode and said second electrode extending axially from said tubular portion.

2. A conductivity sensor as recited in claim 1 wherein said cell has a cell constant defined by the formula:

$$\pi D_2^2 / 4L$$

where $D_2$ is said second inner diameter.

3. A conductivity sensor as recited in claim 1 further comprising a seal material between said first annular electrode and said tubular portion.

4. A conductivity sensor as recited in claim 1 further comprising a control circuit generating an output corresponding to a conductivity of a fluid between said first annular electrode and said second annular electrode.

5. A conductivity sensor as recited in claim 4 wherein said control circuit is an operational amplifier-based.

6. A conductivity sensor as recited in claim 1 further comprising a calibration circuit.

7. A conductivity sensor as recited in claim 6 wherein said calibration circuit comprises a zero adjustment circuit.

8. A conductivity sensor as recited in claim 6 wherein said calibration circuit comprises a gain adjustment circuit.

9. A conductivity sensor as recited in claim 8 wherein said gain adjustment circuit is coupled to said first electrode.

10. A conductivity sensor as recited in claim 1 further comprising a buffer circuit coupled to said first electrode.

11. A conductivity sensor for coupling in a coolant path comprising:

a first annular electrode having a first inner diameter and a first outer diameter, said first annular electrode having a first threaded portion on said first outer diameter;

a second annular electrode having a second inner diameter and a second outer diameter, said second annular electrode having a second threaded portion on said second outer diameter; and a tubular portion disposed axially between said first electrode and said second electrode, said tubular portion having a third inner diameter greater than said first inner diameter and said second inner diameter and substantially equal to said first outer diameter and said second outer diameter;

said tubular portion, said first electrode, and said second electrode defining a sensor cell having said third inner diameter, said cell having a cell length between said first electrode and said second electrode;

said first electrode and said second electrode extending axially from said tubular portion so that said coolant path may be coupled to the first electrode and the second electrode.

12. A sensor as recited in claim 11 wherein said first inner diameter and said second inner diameter are equivalent.

13. A sensor as recited in claim 11 wherein said first outer diameter and said second outer diameter are equivalent.

14. A conductivity sensor as recited in claim 11 further comprising a seal material between said first annular electrode and said tubular portion.

15. A conductivity sensor as recited in claim 11 wherein said seal material comprises polytetrafluoroethylene.

16. A method of assembling a conductivity sensor comprising:

coupling a first annular electrode having a first inner diameter and first outer diameter to a tubular portion having a second inner diameter substantially equal to the first outer diameter;

coupling a second annular electrode having the first inner diameter and the first outer diameter to the tubular portion so that the tubular portion is positioned axially between said first electrode and said second electrode and so that the first electrode and the second electrode extends axially from within the tubular portion, defining a sensor cell having the second inner diameter that is greater than said first inner diameter with said first annular electrode, said second annular electrode, and said tubular portion.

17. A method as recited in claim 16 wherein said step of coupling a first annular electrode having a first inner diameter to a tubular portion comprises threadably coupling a first annular electrode having a first inner diameter to a tubular portion.

18. A method as recited in claim 16 further comprising coupling a control circuit to said first annular electrode and said second annular electrode calibrating the control circuit.

19. A method as recited in claim 18 wherein calibrating said control circuit comprises open circuit zeroing said control circuit.

20. A method as recited in claim 18 wherein calibrating said control circuit comprises adjusting the gain of a buffer circuit.

\* \* \* \* \*